(12) United States Patent
Nitsche et al.

(10) Patent No.: US 8,167,252 B2
(45) Date of Patent: May 1, 2012

(54) CRITICAL CARE EKG LEAD WIRE OR FLUID CONNECTION ORGANIZER

(75) Inventors: Todd Nitsche, Athens, TX (US); William Woods, Rockwall, TX (US); Bader Munir, Karachi (PK); Amy Young, Crowley, TX (US)

(73) Assignee: Medical Component Solutions, LLC, Athens, TX (US)

( * ) Notice: Subject to any disclaimer, the term of this patent is extended or adjusted under 35 U.S.C. 154(b) by 0 days.

(21) Appl. No.: 13/036,754

(22) Filed: Feb. 28, 2011

(65) Prior Publication Data
US 2011/0210215 A1    Sep. 1, 2011

Related U.S. Application Data

(60) Provisional application No. 61/338,927, filed on Feb. 26, 2010.

(51) Int. Cl.
*F16L 3/22* (2006.01)

(52) U.S. Cl. ............. 248/68.1; 5/503.1; 5/658; 24/339; 24/543; 24/562; 224/194

(58) Field of Classification Search ............... 248/68.1, 248/74.1, 74.2, 73, 70, 58, 62; 5/568, 503.1; 224/194

See application file for complete search history.

(56) References Cited

U.S. PATENT DOCUMENTS

| | | | | |
|---|---|---|---|---|
| 4,835,824 A * | 6/1989 | Durham et al. | ........... | 24/339 |
| 5,022,126 A * | 6/1991 | Davis | ........... | 24/543 |
| 5,533,696 A * | 7/1996 | Laughlin et al. | ........... | 248/74.2 |
| 6,116,810 A * | 9/2000 | Eberle | ........... | 403/391 |
| 6,408,492 B1 * | 6/2002 | Sparks et al. | ........... | 24/336 |
| 6,923,407 B2 * | 8/2005 | Takeuchi | ........... | 248/73 |
| 7,179,010 B2 * | 2/2007 | Weger et al. | ........... | 403/289 |

* cited by examiner

*Primary Examiner* — Ramon Ramirez
(74) *Attorney, Agent, or Firm* — DLC Patents, PLLC; Dustin L. Call

(57) ABSTRACT

One example embodiment includes a system for securing a portion of a medical device. The system includes a first arm, where the first arm includes a gripper. The system also includes a second arm. The second arm is attached to the first arm, can move relative to the first arm and includes a gripper. The gripper of the first arm and the gripper of the second arm are configured to grip an external object. The system further includes a fastener, where the fastener is configured to releasably attach the first arm to the second arm, and a holder, where the holder is configured to hold at least a portion of a medical device.

20 Claims, 6 Drawing Sheets

CRITICAL CARE EKG LEAD WIRE OR FLUID CONNECTION ORGANIZER

CROSS-REFERENCE TO RELATED APPLICATIONS

This application claims the benefit of and priority to U.S. Provisional Patent Application Ser. No. 61/338,927 filed on Feb. 26, 2010, which application is incorporated herein by reference in its entirety.

BACKGROUND OF THE INVENTION

Medical technology has improved dramatically in recent history and this improvement continues unabated. Diseases which were once considered fatal are now routinely treatable. Often, a patient which would have been given up as terminal can now be treated for a few days or even a few hours and then released to recover at home.

Often, in the course of medical treatment, a patient is connected to a medical device. These medical devices can be as simple as an IV line to provide fluids or blood to the patient or as complex as an EKG machine which has multiple leads hooked to the patient each giving important feedback regarding the patient's condition. Sometimes, the time that it takes to connect these medical devices is critical. For example, when attaching lead wires to an EKG monitor, the leads may become entangled and cause a delay in hooking them up to the patient. This delay can be prevent the doctor or other caregiver from obtaining much needed information or otherwise delay treatment. This can, in turn, hamper the quality and timeliness of care which the patient receives.

Additionally, without sufficient support, the lead wires or fluid connections may become detached from the patient and cause unnecessary patient treatment or feedback. In particular, many times the wires and tubes connecting the patient to critical care machines simply are draped over the patient's bed and then hang between the bed and the device. This can lead to problems as the weight of the tubing and/or wires can provide a force which tends to detach the device from the patient.

To prevent detaching the tubes or wires are often wrapped around a portion of the patient's bed. This helps support the weight of the tubes or wires, but restricts movement of the patient. For example, if the patient rolls over or is moved, the leads may then detach from the patient. I.e., hooking the leads to the bed can often help cause the very problem that it is intended to avoid.

Accordingly, there is a need in the art for a device which can prevent tangles in the connections from the patient to the medical device. Additionally, there is a need for the device to allow the patient freedom of movement. Further, there is a need in the art for the device to support the weight of the connections.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

One example embodiment includes a system for securing a portion of a medical device. The system includes a first arm, where the first arm includes a gripper. The system also includes a second arm. The second arm is attached to the first arm, can move relative to the first arm and includes a gripper. The gripper of the first arm and the gripper of the second arm are configured to grip an external object. The system further includes a fastener, where the fastener is configured to releasably attach the first arm to the second arm, and a holder, where the holder is configured to hold at least a portion of a medical device.

Another example embodiment includes a system for securing a portion of a medical device. The system includes a body. The body includes a head and a first arm. The first arm is attached to the head, can move relative to the head and includes a gripper. The body also includes a second arm. The second arm is attached to the head, can move relative to the head and includes a gripper. The gripper of the first arm and the gripper of the second arm are configured to grip an external object. The system also includes a fastener, where the fastener is configured to releasably attach the first arm to the second arm, and a holder, where the holder is configured to hold at least a portion of a medical device.

Another example embodiment includes a system for securing a portion of a medical device. The system includes a body. The body includes a head and a first arm. The first arm is attached to the head, can move relative to the head and includes a gripper. The body also includes a second arm. The second arm is attached to the head, can move relative to the head and includes a gripper. The gripper of the first arm and the gripper of the second arm are configured to grip an external object. The system also includes a fastener, where the fastener is configured to releasably attach the first arm to the second arm, and a release, where the release is configured to release the fastener. The system further includes a holder. The holder is attached to the head and includes four slots, where each of the four slots is configured to hold at least a portion of a medical device.

These and other objects and features of the present invention will become more fully apparent from the following description and appended claims, or may be learned by the practice of the invention as set forth hereinafter.

BRIEF DESCRIPTION OF THE DRAWINGS

To further clarify various aspects of some example embodiments of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF SOME EXAMPLE EMBODIMENTS

Reference will now be made to the figures wherein like structures will be provided with like reference designations. It is understood that the figures are diagrammatic and schematic representations of some embodiments of the invention, and are not limiting of the present invention, nor are they necessarily drawn to scale.

Figure 1A:
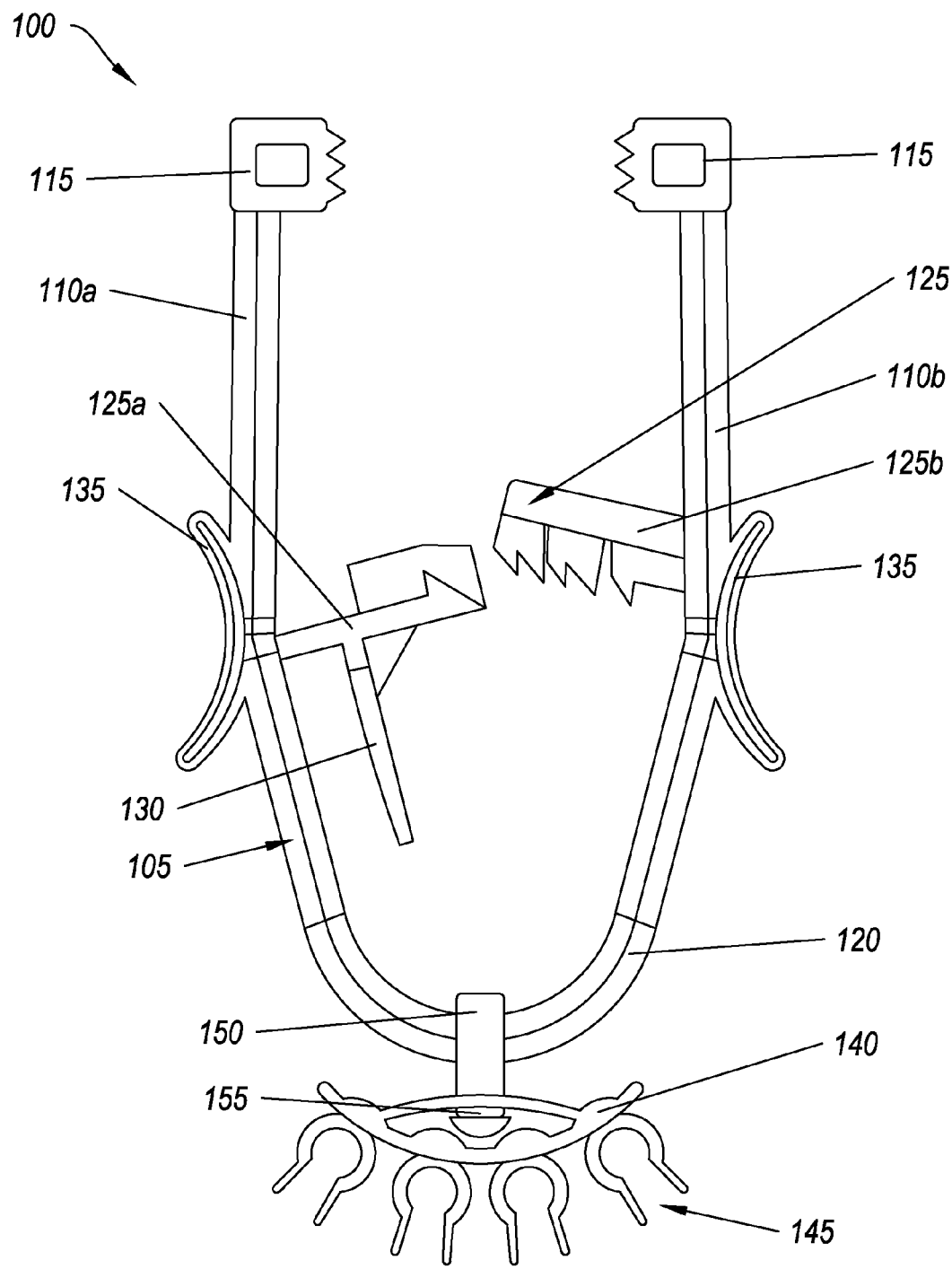
FIG. 1A illustrates a top view of a system for securing a portion of a medical device.
Figure 1B:
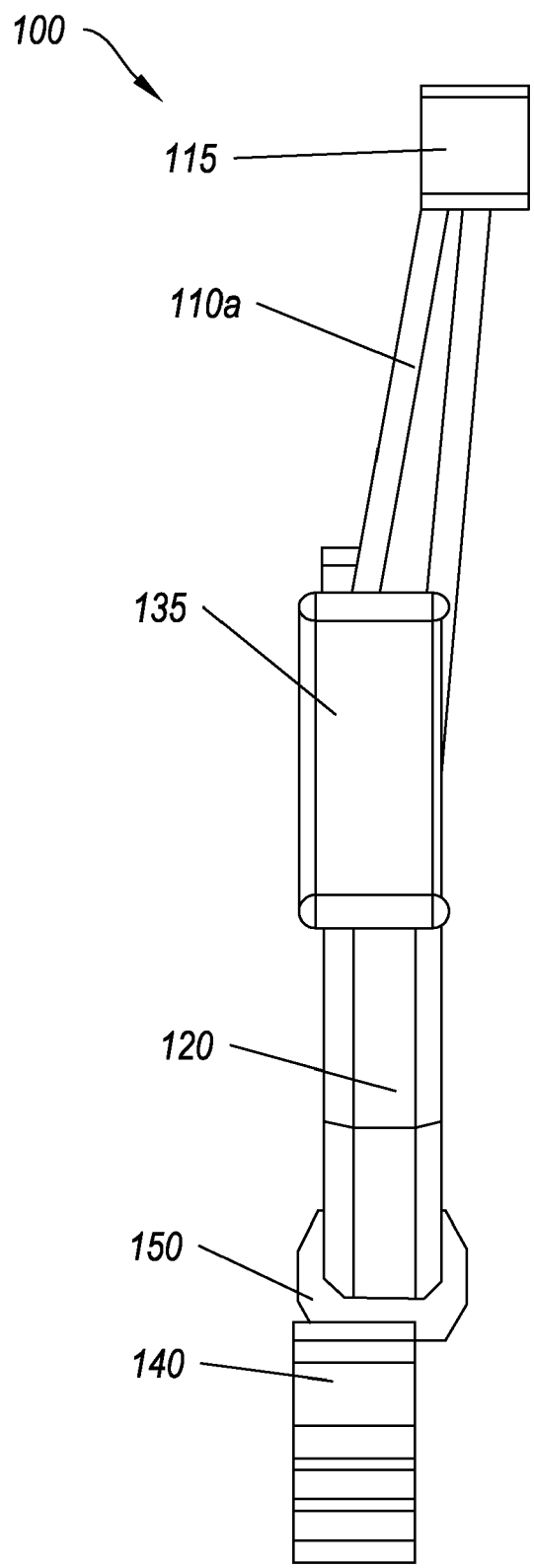
FIG. 1B illustrates a side view of the system for securing a portion of a medical device.
Figure 1C:
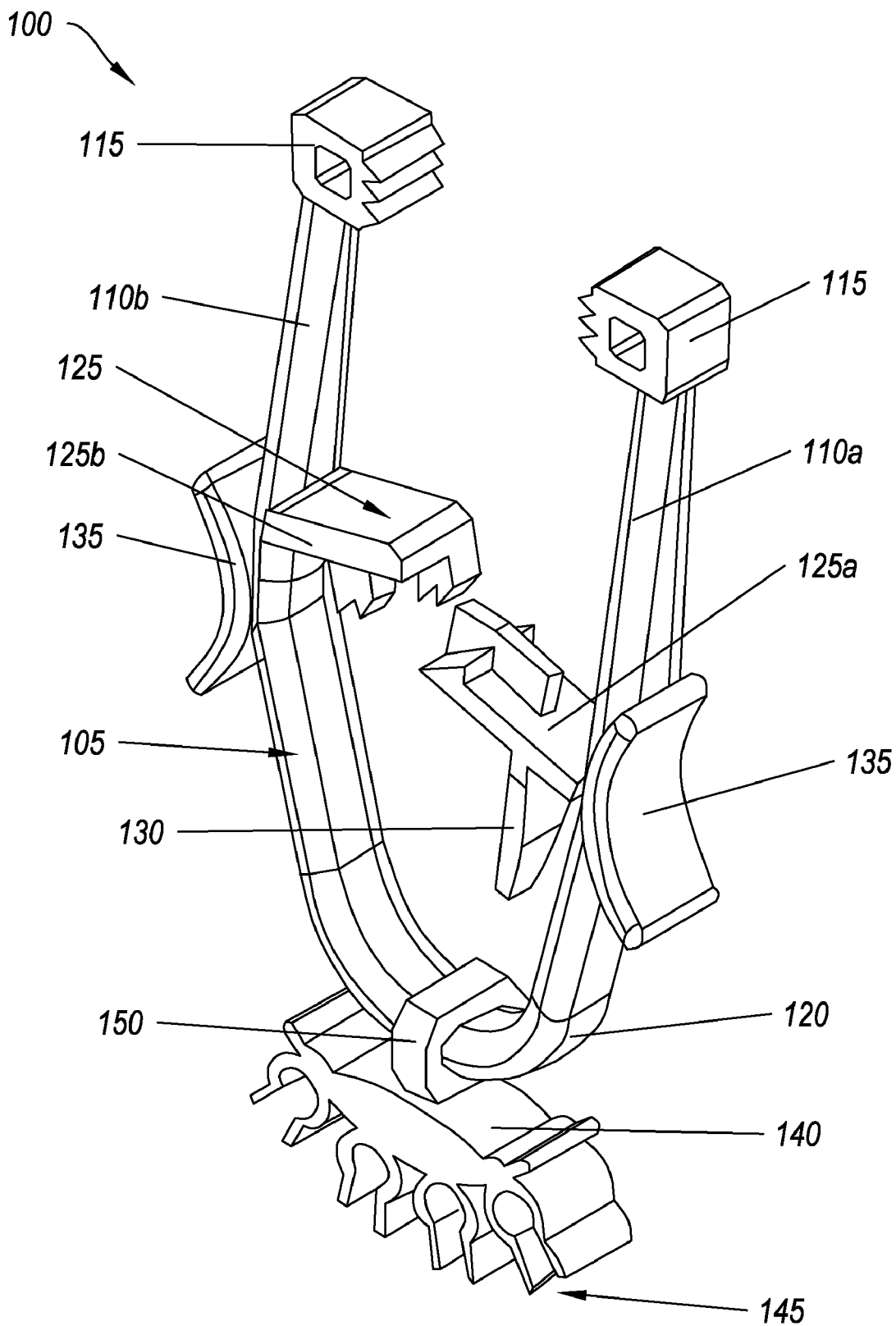
FIG. 1C illustrates a perspective view of the system for securing a portion of a medical device.

FIGS. 1A, 1B and 1C illustrate an example of a system 100 for securing a portion of a medical device. FIG. 1A illustrates a top view of the system 100 for securing a portion of a medical device; FIG. 1B illustrates a side view of the system 100 for securing a portion of a medical device; and FIG. 1C illustrates a perspective view of the system 100 for securing a portion of a medical device. In at least one implementation, the portion of the medical device can include wiring, leads or tubing connected to a medical device. For example, the system 100 can be used to organize EEG or EKG wiring. Additionally or alternatively, the system 100 can be used to organize tubes, such as IV tubing or other medical tubing that will be used on a patient. In particular, the system 100 can be used to ensure that the tubes, leads and/or wires remain in a stable position relative to one another and relative to the patient.

FIGS. 1A, 1B and 1C show that the system 100 includes a body 105. In at least one implementation, the body 105 can allow the system 100 to connect to an external object, such as bedding, clothing, railing or furniture. This can, in turn, ensure that the position of system 100 remains constant relative to the external object as desired by the user, as described below. Additionally or alternatively, the body 105 can ensure that the position of the other parts of the system 100 remain stable relative to one another.

In at least one implementation, the body 105 can be made of lightweight materials. For example, the body can be made of plastic. One of skill in the art will appreciate that making the body 105 of lightweight materials can minimize the any discomfort experienced by the patient. For example, if the system 100 is attached to the patient's clothing, then a lightweight system 100 is more likely to minimize the discomfort experienced by the patient.

FIGS. 1A, 1B and 1C show that the body 105 can include a first arm 110a and a second arm 110b (collectively "arms 110"). In at least one implementation, the arms 110 are configured to move relative to one another. This can allow the system 100 to be attached to an external object, as described below. Further, the first arm 110a and the second arm 110b can be locked into position relative to one another, as described below.

In at least one implementation, the arms 110 can be between 1.2 and 2.0 inches apart from one another. For example, the arms 110 can be approximately 1.6 inches apart from one another. Additionally or alternatively, the arms 110 can be between 2.1 inches and 3.3 inches long. For example, the arms 110 can be approximately 2.7 inches long. Additionally or alternatively, the arms 110 can be between 0.2 inches in diameter and 0.3 inches in diameter. For example, the arms 110 can be approximately 0.25 inches in diameter. As used in the specification and the claims, the term approximately shall mean that the value is within 10% of the stated value, unless otherwise specified.

FIGS. 1A, 1B and 1C show that the arms 110 can include a gripper 115. In at least one implementation, the gripper 115 can be used to grip an external object. For example, the gripper 115 can be used to grip a patient's clothing or bedding or furniture, such as a bed frame, bed railing, stretcher railing or wheel chair. Additionally or alternatively, the gripper 115 can be used to attach external objects to one another. For example, the gripper 115 can be used to attach a cloth to the patient's clothing during surgery. One of skill in the art will appreciate that the gripper 115 can directly grip the external object or can be used to enclose the external object.

FIGS. 1A, 1B and 1C also show that the body 105 includes a head 120. In at least one implementation, the first arm 110a and the second arm 110b can each be attached to the head 120 I.e., the head 120 can maintain a proper separation of the first arm 110a relative to the second arm 110b. Additionally or alternatively, the head 120 can allow the arms 110 to move relative to one another. I.e., the attachment of the arms 110 to the head 120 can allow the arms 100 to move relative to the head 120 and, therefore, relative to one another. In particular, the head 120 can provide stable pivot points for the arms 110 which can allow the gripper 115 to be closed and, therefore, engage the external object.

One of skill in the art will appreciate that the arms 110 and the head 120 need not be distinct parts attached to one another. For example, FIGS. 1A, 1B and 1C show that the arms 110 and the head 120 can form a single "U" shape which provides the functionality described above. I.e., the arms 110 and the head 120 can be a single piece of material that provides the desired functionality.

FIGS. 1A, 1B and 1C further show that the body 105 can include a fastener 125. In at least one implementation, the fastener 125 is configured to hold the position of the first arm 110a relative to the second arm 110b. I.e., the fastener 125 can attach the first arm 110a to the second arm 110b. Holding the position of the first arm 110a relative to the second arm 110b can allow the system 100 to be attached to an external object, as described below. In particular, holding the position of the first arm 110a relative to the second arm 110b can provide a force which keeps the gripper 115 engaged with the external object.

In at least one implementation, the fastener 125 can include a first portion 125a attached to the first arm 110a and a second portion 125b attached to the second arm 110b. In particular, the first portion 125a can releasably attach to the second portion 125b, as desired by the user. For example, the first portion 125a can include a ridged surface. The second portion 125b can also include a ridged portion which is configured to come in contact with the ridged portion of the first portion 125a such that the ridged portions will lock into place relative to one another. The presence of the ridges can allow the fastener 125 to ratchet. I.e., the ridges can allow the user to use more or less force when using the fastener 125 to hold the position of the first arm 110a relative to the second arm 110b. This can, in turn, allow the user to determine how much force will be used when attaching the system 100 to the external object, as described below.

FIGS. 1A, 1B and 1C also show that the body 105 can include a release 130. In at least one implementation, the release 130 can detach the first portion 125a from the second portion 125b. I.e., the release 130 can release the fastener 125 such that the first arm 110a and the second arm 110b can move relative to one another. For example, the release 130 can include a lever which moves the ridges of the first portion 125a away from the ridges of the second portion 125b so that they no longer engage one another.

FIGS. 1A, 1B and 1C further show that the body 105 can include one or more pads 135. In at least one implementation, the pads 135 can be used to move the arms 110 toward one another. In particular, the pads 135 can accommodate the fingers of the user and allow the user to push on the pads 135 which moves the first arm 110a and the second arm 110b toward one another. In addition, the pads 135 can allow the user to apply sufficient force to engage the fastener 125.

FIGS. 1A, 1B and 1C also show that the system 100 can include a holder 140. In at least one implementation, the holder 140 can be used to attach the system 100 to a portion of a medical device. For example, the holder 140 can be used to retain wires or medical tubing. In particular, the holder 140 can include one or more slots 145. A portion of the medical device can be inserted into one of the slots 145 where it is retained.

In at least one implementation, the one or more slots 145 can include a rounded portion or other configurations configured to hold the desired portion of the medical device. For example, the slots 145 can include rounded portions of different diameters to accommodate portions of medical devices which have differing diameters. One of skill in the art will appreciate that the slots 145 can be similar to one another or different from one another, as desired by the user.

FIGS. 1A, 1B and 1C further show that the holder 140 can include an attachment 150. In at least one implementation, the attachment 150 can releasably attach the holder 140 to the head 120. For example, the attachment 150 can include a clip or other attachment mechanism. The attachment 150 can allow the holder 140 to be removed and changed for a different holder 140. Changing the holder 140 can allow a single body 105 to be used, even if the medical device to be retained changes over the course of a patient's treatment.

FIGS. 1A, 1B and 1C also show that the attachment 150 can include a swivel 155. In at least one implementation, the swivel 155 can allow the holder 140 to move relative to the body 105 without the need to detach the holder 140. In particular, as the patient moves, the medical device, or portions thereof, are allowed to move to accommodate the patient's movements without causing discomfort and without a need to move the system 100.

Figure 2:
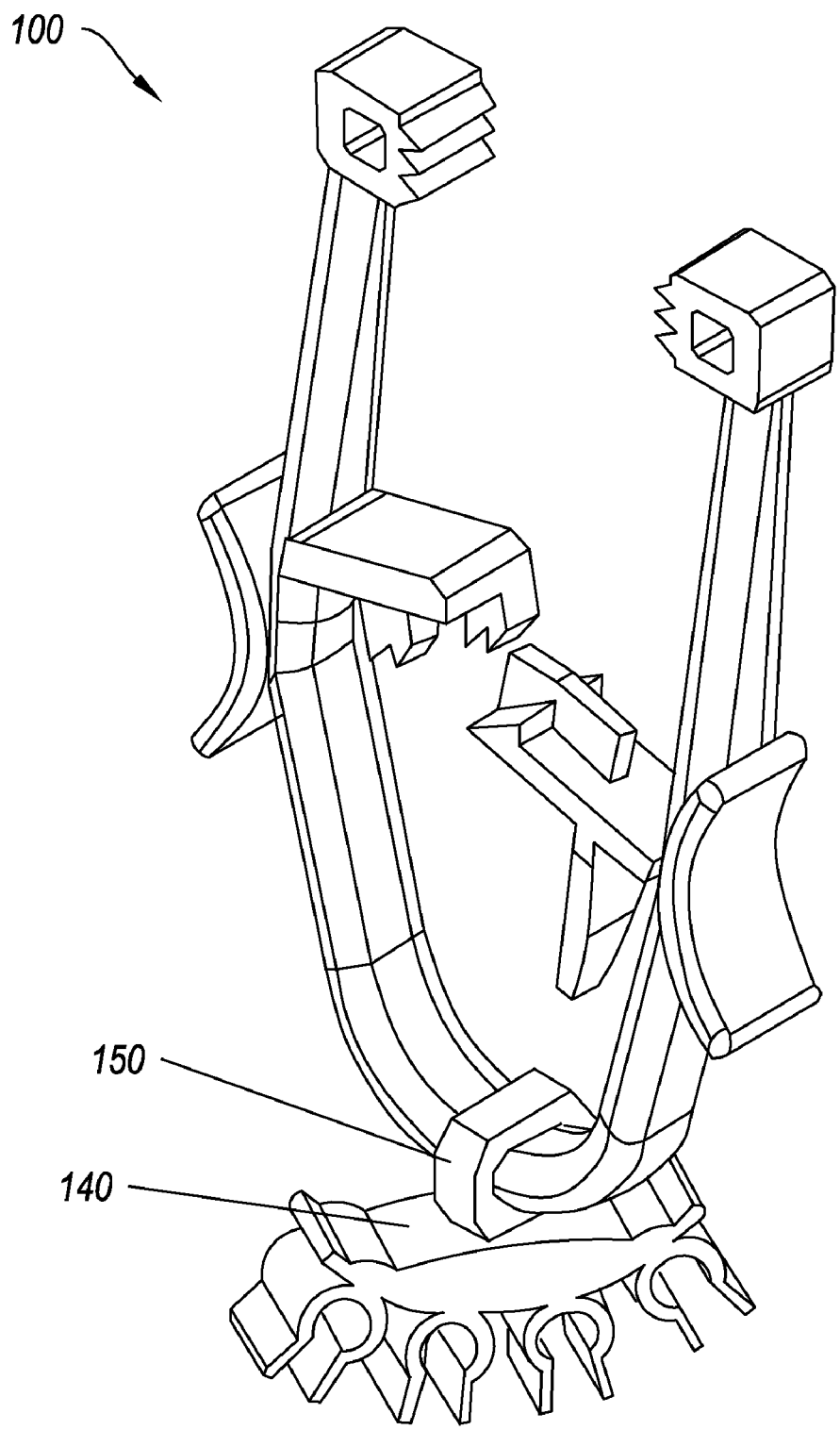
FIG. 2 illustrates an alternative view of the system for securing a portion of a medical device.

FIG. 2 illustrates an alternative view of the system 100 for securing a portion of a medical device. In at least one implementation, the system 100 allows the patient some freedom of movement. In particular, even though the system 100 is configured to hold at least a portion of a medical device, the system can allow the portion of the medical device to move within the system 100. Additionally or alternatively, the system 100 can adjust to the position of the patient, as described below.

FIG. 2 shows that the holder 140 can rotate about the attachment 150. In at least one implementation, rotation of the holder 140 can increase the freedom of movement of the patient. Additionally or alternatively, rotation of the holder 140 can increase the comfort level of the patient. In particular, as the patient moves, the portion of the medical device, which is connected to the patient, within the holder moves. This movement can be accommodated by rotation of the holder 140 about the attachment 150.

Figure 3:
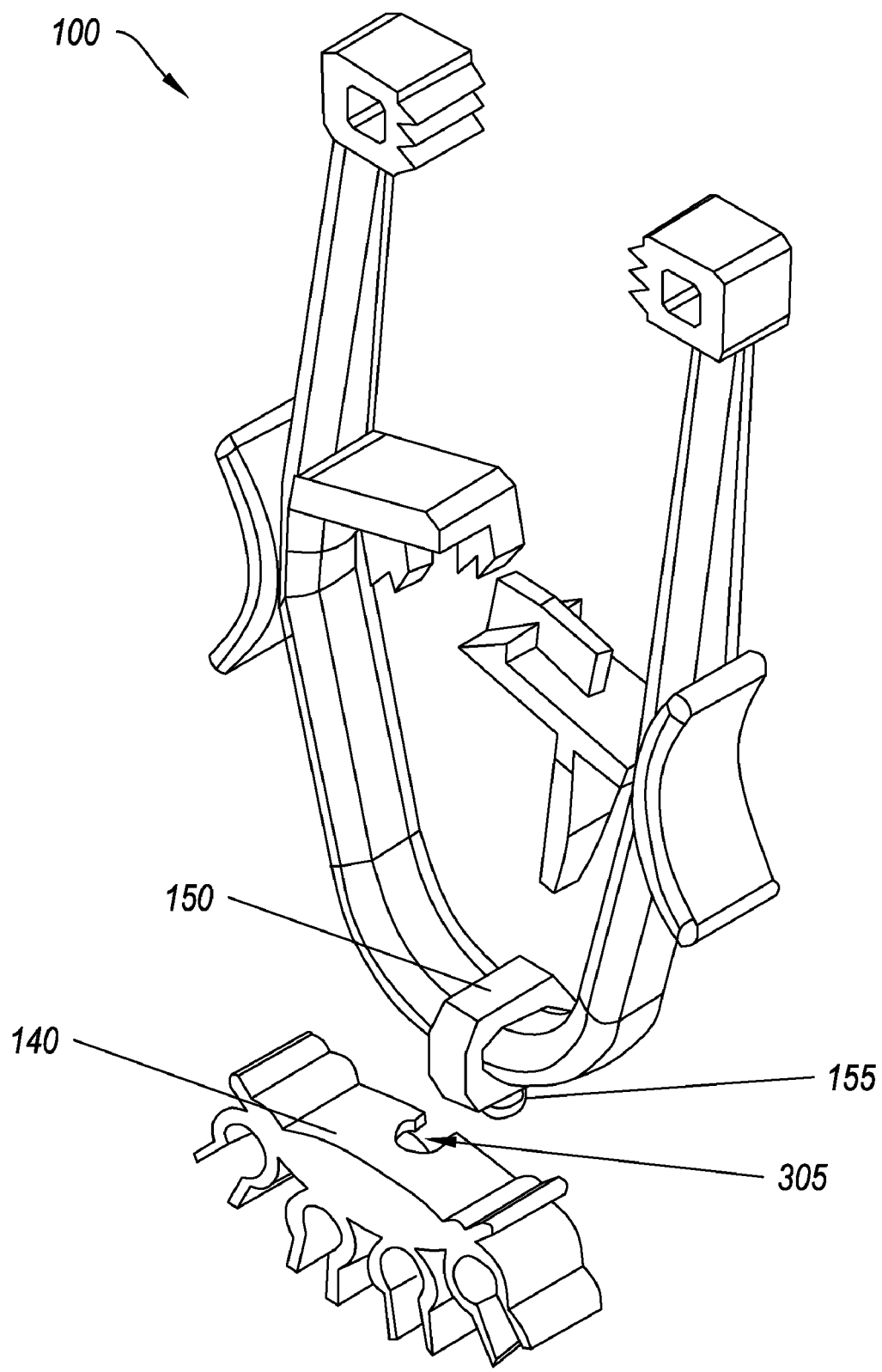
FIG. 3 illustrates an exploded view of the system for securing a portion of a medical device.

FIG. 3 illustrates an exploded view of the system 100 for securing a portion of a medical device. In at least one implementation, the system 100 can have parts interchanged in order to accommodate portions of medical devices which are of different sizes. In particular, medical devices can require different attachment methods. Even similar devices manufactured by different suppliers can require different attachment methods. Allowing interchangeable parts can allow the system 100 to accommodate different medical devices.

FIG. 3 shows that that the holder 140 can include an opening 305. In at least one implementation, the opening 305 is configured to snap around the swivel 155. One of skill in the art will appreciate that snapping the swivel 155 into the opening 305 can allow the holder 140 to rotate relative to the attachment 150. Additionally or alternatively, snapping the swivel 155 into the opening 305 can allow the holder 140 to be changed for a holder of different size or configuration, as needed.

Figure 4:
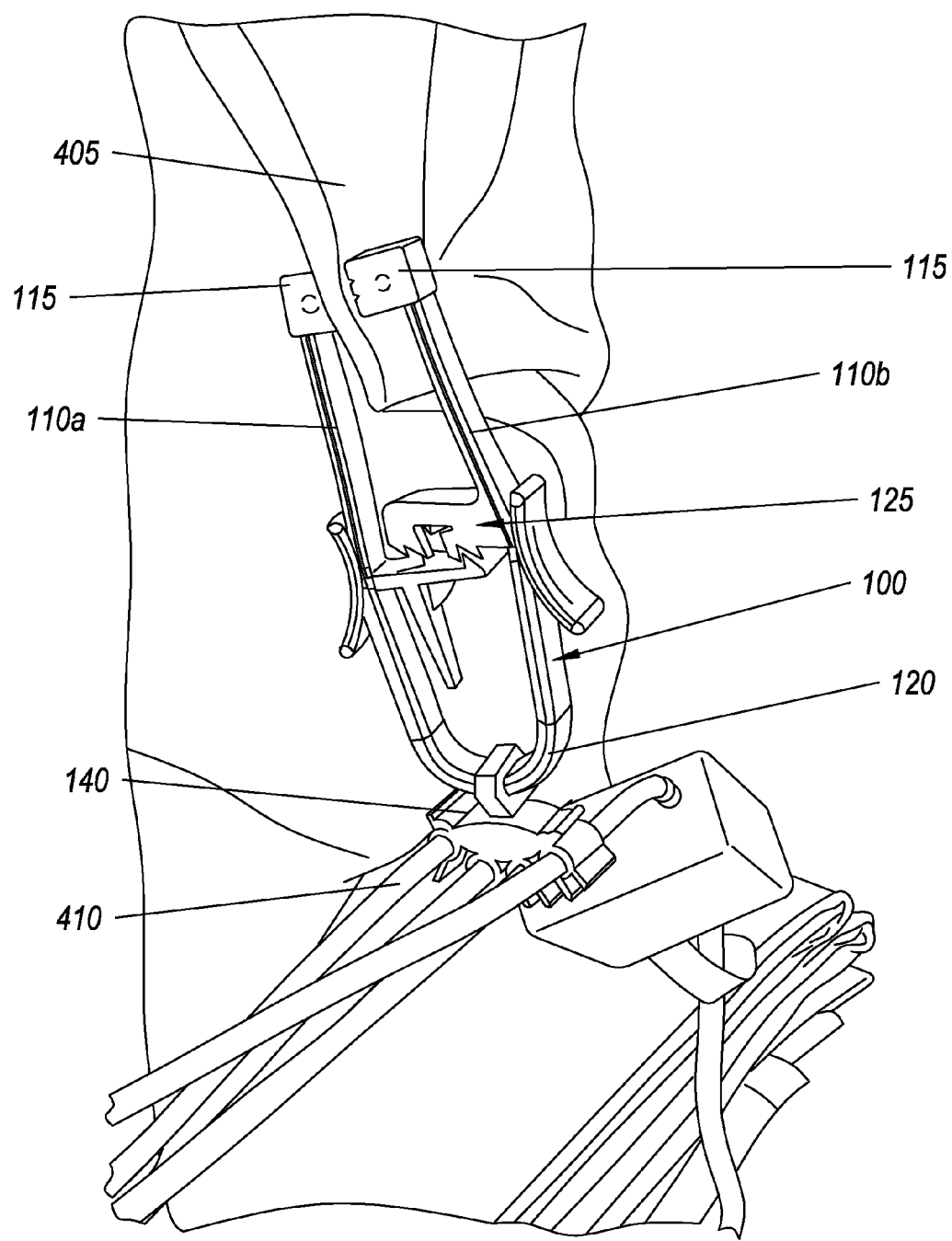
FIG. 4 illustrates an example of the system for securing a portion of a medical device with the fastener engaged.

FIG. 4 illustrates an example of the system 100 for securing a portion of a medical device with the fastener 125 engaged.

In at least one implementation, when the fastener 125 is engaged, the first arm 110*a* and the second arm 110*b* are held in position relative to one another. I.e., the position of the first arm 110*a* and the second arm 110*b* relative to the head 120 is modified allowing the ends of the first arm 110*a* and the second arm 110*b* to approach one another and the gripper 115 to engage an external object.

FIG. 4 shows that the fastener 125 is engaged to hold the first arm 110*a* and the second arm 110*b* in position relative to one another. With the fastener 125 engaged, the gripper 115 can grip and hold the patient's bedding 405. I.e., the position of the system 100 can be held constant relative to the bedding 405 by the gripper 115. One of skill in the art will appreciate that the gripper 115 can be used to grip and hold any external object and that the bedding 405 is shown for illustrative purposes only.

FIG. 4 also shows that the holder 140 can retain a portion of a medical device 410. In at least one implementation, the system 100 can be used with multiple portions of a single medical device 410 or with portions of multiple medical devices 410. For example, an EKG machine can include ten or more leads which are attached to the patient for monitoring purposes. The holder 140 can retain some or all of the leads attached to a single patient. Alternatively, the holder 140 can retain an IV tube, a catheter tube and an EKG lead. One of skill in the art will appreciate that the examples provided herein are illustrative only and any combination is within the scope of the invention as disclosed herein.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for securing a portion of a medical device, the system comprising:
   a head;
   a first arm, wherein the first arm:
      is attached to the head;
      can move relative to the head; and
      includes a gripper;
   a second arm, wherein the second arm:
      is attached to the head
      can move relative to the head; and
      includes a gripper;
   wherein the gripper of the first arm and the gripper of the second arm are configured to grip an external object;
   a fastener, wherein the fastener is configured to releasably attach the first arm to the second arm;
   a holder, wherein the holder is configured to hold at least a portion of a medical device; and
   an attachment, wherein the attachment is configured to releasably attach the holder to the head.

2. The system of claim 1, further comprising fastening means, wherein the fastening means is configured to hold the position of the second arm relative to the second arm.

3. The system of claim 1, wherein the holder includes slots.

4. The system of claim 3, wherein the holder includes four slots.

5. The system of claim 1, wherein the holder includes an open rounded portion.

6. The system of claim 5, wherein the holder includes three rounded portions, wherein each rounded portion has a different diameter.

7. The system of claim 5, wherein the rounded portion is configured to hold medical tubing.

8. The system of claim 5, wherein the rounded portion is configured to hold wiring.

9. The system of claim 1, wherein the external object includes clothing.

10. The system of claim 1, wherein the external object includes bedding.

11. A system for securing a portion of a medical device, the system comprising:
   a body, wherein the body includes:
      a head;
      a first arm, wherein the first arm:
         is attached to the head;
         can move relative to the head; and
         includes a gripper;
      a second arm, wherein the second arm:
         is attached to the head;
         can move relative to the head; and
         includes a gripper;
      wherein the gripper of the first arm and the gripper of the second arm are configured to grip an external object;
   a fastener, wherein the fastener is configured to releasably attach the first arm to the second arm;
   a holder, wherein the holder is configured to hold at least a portion of a medical device; and
   an attachment, wherein the attachment:
      is configured to releasably attach the holder to the head; and includes:
         an attachment body, wherein the attachment body is configured to attach to the head; and
         a swivel, wherein the swivel is configured to be at least partially inserted into an opening in the holder.

12. The system of claim 11, wherein the gripper of the first arm includes a ridged surface.

13. The system of claim 11, wherein the gripper of the first arm is located opposite the attachment of the first arm to the head.

14. The system of claim 13, wherein the gripper of the second arm is located opposite the attachment of the second arm to the head.

15. A system for securing a portion of a medical device, the system comprising:
   a body, wherein the body includes:
      a head;
      a first arm, wherein the first arm:
         is attached to the head;
         can move relative to the head; and
         includes a gripper;
      a second arm, wherein the second arm:
         is attached to the head;
         can move relative to the head; and
         includes a gripper;
      wherein the gripper of the first arm and the gripper of the second arm are configured to grip an external object;
   a fastener, wherein the fastener is configured to releasably attach the first arm to the second arm;
   a release, wherein the release is configured to release the fastener;
   a holder, wherein the holder:
      is attached to the head; and
      includes four slots, wherein each of the four slots is configured to hold at least a portion of a medical device; and
   an attachment, wherein the attachment is configured to releasably attach the holder to the head.

16. The system of claim 15, wherein the release includes a lever.

17. The system of claim 15 further comprising:
   a first pad on the first arm; and
   a second pad on the second arm;
   wherein the first pad and the second pad are configured to allow a user to push the first arm and the second arm toward one another.

18. The system of claim 15, wherein the fastener includes a first portion attached to the first arm.

19. The system of claim 18, wherein the fastener includes a second portion attached to the second arm.

20. The system of claim 19, wherein:
   the first portion of the fastener includes a ridged portion;
   the second portion of the fastener includes a ridged portion; and
   the ridged portion on the first portion of the fastener is configured to engage the ridged portion on the second portion of the fastener.

* * * * *